(12) United States Patent
Singh et al.

(10) Patent No.: US 8,311,624 B2
(45) Date of Patent: Nov. 13, 2012

(54) APPARATUS AND METHOD FOR DELIVERING A THERAPEUTIC AGENT TO OCULAR TISSUE

(75) Inventors: Rishi P. Singh, Shaker Heights, OH (US); Vadim F. Lvovich, Cleveland Heights, OH (US); Brian L. Davis, Moreland Hills, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 270 days.

(21) Appl. No.: 12/567,653

(22) Filed: Sep. 25, 2009

(65) Prior Publication Data

US 2010/0137780 A1    Jun. 3, 2010

Related U.S. Application Data

(63) Continuation-in-part of application No. 11/874,859, filed on Oct. 18, 2007.

(60) Provisional application No. 61/100,464, filed on Sep. 26, 2008, provisional application No. 60/829,978, filed on Oct. 18, 2006.

(51) Int. Cl.
*A61N 1/30* (2006.01)
*A61M 35/00* (2006.01)

(52) U.S. Cl. .......... 604/20; 604/289; 604/294; 604/295; 604/300

(58) Field of Classification Search .......... 604/20, 604/294, 501, 521, 289, 290, 295, 300, 301, 604/302
See application file for complete search history.

(56) References Cited

U.S. PATENT DOCUMENTS

| 6,009,345 | A | 12/1999 | Hofmann |
| 6,319,240 | B1 | 11/2001 | Beck |
| 6,512,950 | B2 | 1/2003 | Li et al. |
| 6,553,255 | B1 | 4/2003 | Miller et al. |
| 6,801,804 | B2 * | 10/2004 | Miller et al. ............ 604/20 |
| 6,929,949 | B1 | 8/2005 | Hoff et al. |
| 7,137,975 | B2 | 11/2006 | Miller et al. |
| 7,503,605 | B2 * | 3/2009 | Mears .................. 294/1.2 |
| 2002/0010414 | A1 | 1/2002 | Coston et al. |
| 2004/0176803 | A1 | 9/2004 | Whelan et al. |
| 2005/0148996 | A1 * | 7/2005 | Sun et al. .............. 604/501 |

(Continued)

FOREIGN PATENT DOCUMENTS

WO  WO-2008/063338 A2  5/2008

*Primary Examiner* — Kevin C Sirmons
*Assistant Examiner* — Shefali Patel
(74) *Attorney, Agent, or Firm* — Tarolli, Sundheim, Covell & Tummino LLP

(57) ABSTRACT

An apparatus for delivering at least one therapeutic agent to an ocular tissue of a subject includes at least one electrode, a medicament layer including the at least one therapeutic agent, an electrical signal source, and logic configured to control the electrical signal source. The at least one electrode has oppositely disposed, dome-shaped first and second major surfaces. The first major surface is curved such that the first major surface substantially conforms to a contour of the ocular tissue when placed in contact with the ocular tissue. The medicament layer is disposed on at least a portion of the second major surface. The electrical signal source provides a signal having certain characteristics and is electrically connected to the at least one electrode. The certain characteristics comprise at least one orienting frequency and at least one motivating frequency sufficient to motivate the at least one therapeutic agent into the ocular tissue.

8 Claims, 14 Drawing Sheets

U.S. PATENT DOCUMENTS

| | | |
|---|---|---|
| 2005/0181018 A1 | 8/2005 | Peyman |
| 2005/0245856 A1* | 11/2005 | Roy ............................... 604/20 |
| 2005/0273046 A1 | 12/2005 | Kwiatkowski et al. |
| 2007/0082841 A1 | 4/2007 | Higuchi et al. |
| 2007/0106278 A1* | 5/2007 | Higuchi et al. ............ 604/891.1 |
| 2007/0123814 A1 | 5/2007 | Roy |
| 2007/0299386 A1 | 12/2007 | Peyman |
| 2007/0299420 A1 | 12/2007 | Peyman |
| 2008/0009471 A1 | 1/2008 | Higuchi et al. |

* cited by examiner

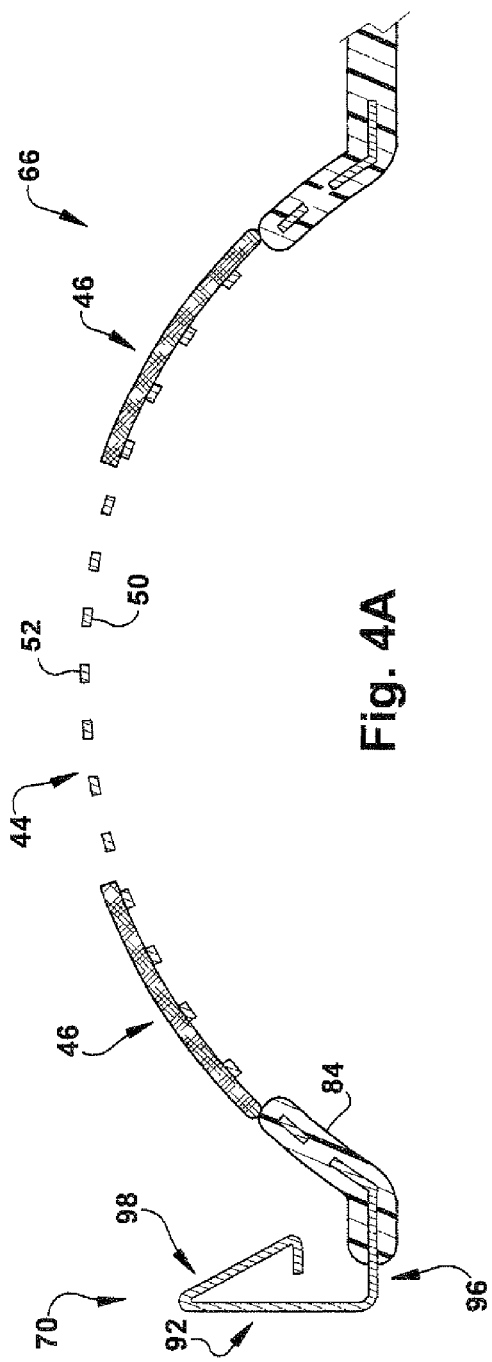
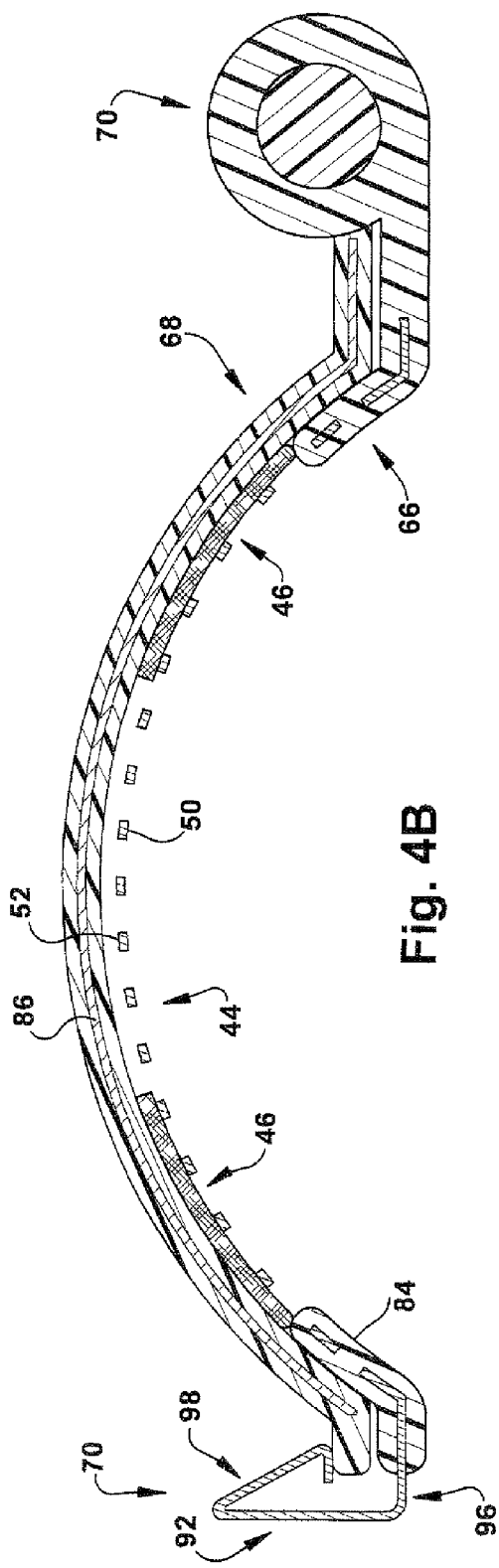

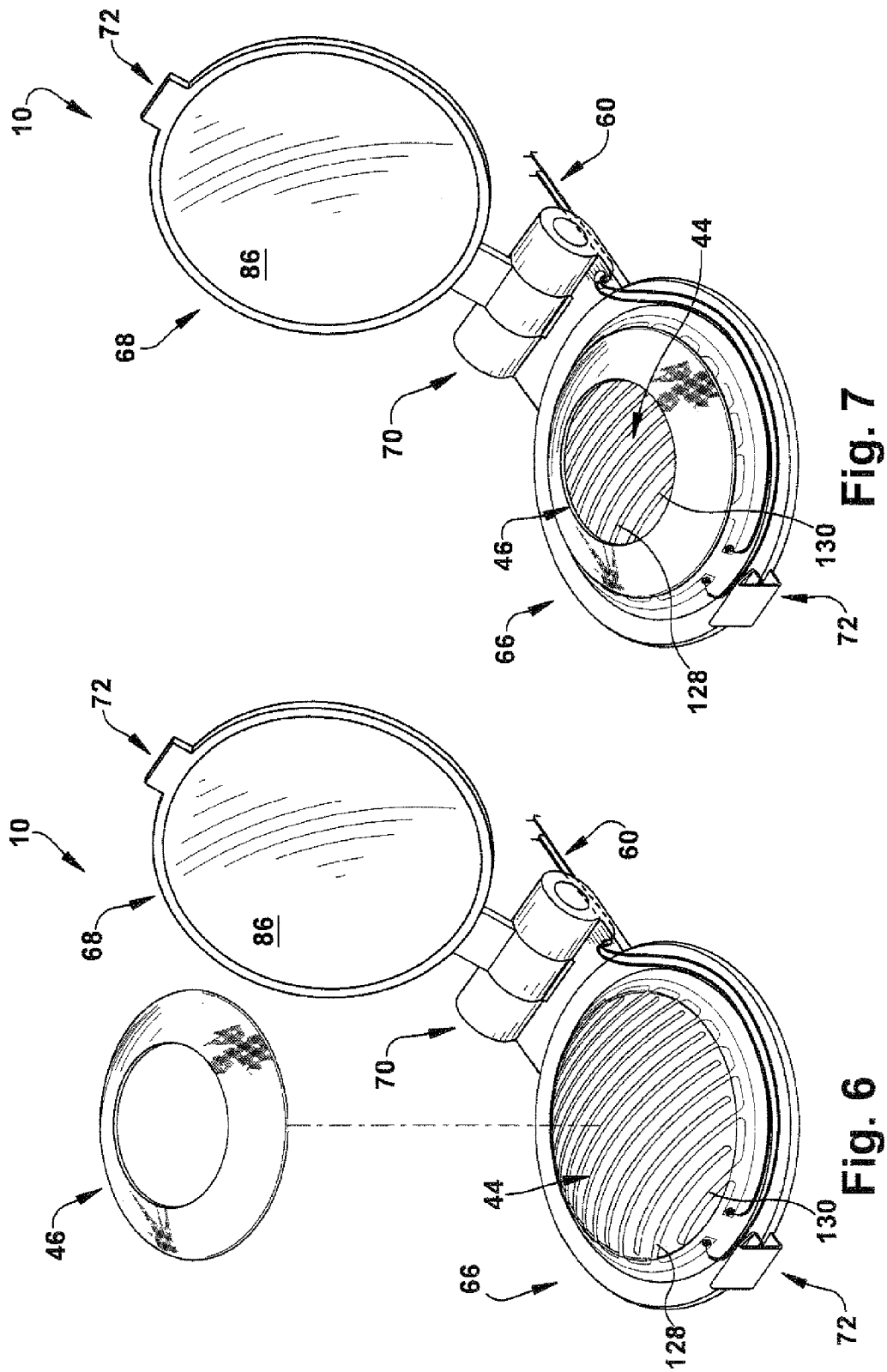

APPARATUS AND METHOD FOR DELIVERING A THERAPEUTIC AGENT TO OCULAR TISSUE

RELATED APPLICATIONS

This application claims priority from U.S. Provisional Patent Application Ser. No. 61/100,464, filed Sep. 26, 2008, and is a continuation-in-part of U.S. patent application Ser. No. 11/874,859, filed Oct. 18, 2007, which claims priority from U.S. Provisional Patent Application Ser. No. 60/829,978, filed on Oct. 18, 2006 (now expired). The subject matter of the aforementioned applications is hereby incorporated by reference in their entireties.

TECHNICAL FIELD

The present invention relates generally to an apparatus and method for delivering a therapeutic agent to ocular tissue, and more particularly to a dielectrophoretic apparatus and related method for delivering at least one therapeutic agent to an ocular tissue of a subject.

BACKGROUND OF THE INVENTION

The treatment of ocular diseases in mammals, including humans and non-humans alike often requires that drugs or other agents be delivered to the eye in a therapeutic dose. Such diseases may occur in the choroid, the retina, the crystalline lens, and the optic nerve, as well as other ocular structures. One treatment methodology is to deliver an ocular agent to these structures via local drug administration, as opposed to systemic drug administration. This permits agents to be delivered directly to a site requiring evaluation and/or therapy. Because of drug localization, there is less of a concern for release or dissemination of the drug beyond the site of delivery. Such is also the case for other body sites where it is desirable to limit drug dissemination or systemic administration, yet still provide drugs in various formulations.

In many instances, however, local drug administration to the eye is not easily accomplished. Thus, localized drug administration often requires rather invasive procedures to gain access to the various ocular structures being treated. This may entail inserting a conduit, such as a fine gauge needle into the eye, or forming an incision for positioning of a device, such as a drug depot. Consequently, such treatment typically requires a visit to a hospital or doctor's office where trained health care professionals can perform the necessary, relatively more invasive procedures to achieve local drug administration.

Another form of localized drug delivery may be accomplished using iontophoresis. Although iontophoresis is generally well-accepted by patients and medical professionals, there are some risks involved. For example, high current intensity or long treatment times can lead to pain, burning sensations, skin irritation, erythema, blister formation, and skin necrosis. In the most extreme cases, high currents produced by direct current iontophoresis can short through a patient's heart. Iontophoresis also requires reformulated compounds for application and, thus, cannot typically use market-available drugs.

SUMMARY OF THE INVENTION

According to one aspect of the present invention, an apparatus is provided for delivering at least one therapeutic agent to an ocular tissue of a subject. The apparatus comprises at least one electrode, a medicament layer including the at least one therapeutic agent, an electrical signal source, and logic configured to control the electrical signal source. The at least one electrode has oppositely disposed, dome-shaped first and second major surfaces. The first major surface is curved such that the first major surface substantially conforms to the contour of the ocular tissue when the first major surface is in contact with the ocular tissue. The medicament layer is disposed on at least a portion of the second major surface. The electrical signal source is for providing a signal having certain characteristics. The electrical signal source is electrically connected to the at least one electrode. The certain characteristics of the electrical signal source comprise at least one orienting frequency and at least one motivating frequency sufficient to motivate the at least one therapeutic agent into the ocular tissue.

According to another aspect of the present invention, a system is provided for delivering at least one therapeutic agent to an ocular tissue of a subject. The system comprises an apparatus, an electrical lead, and a displacement device. The apparatus comprises at least one electrode, a medicament layer, an electrical signal source, and logic configured to control the electrical signal source. The at least one electrode has oppositely disposed, dome-shaped first and second major surfaces. The first major surface is curved such that the first major surface substantially conforms to the contour of the ocular tissue when the first major surface is in contact with the ocular tissue. The medicament layer is disposed on at least a portion of the second major surface. The electrical signal source is for providing a signal having certain characteristics. The electrical signal source is electrically connected to the at least one electrode. The certain characteristics of the electrical signal source comprise at least one orienting frequency and at least one motivating frequency sufficient to motivate the at least one therapeutic agent into the ocular tissue. The electrical lead includes oppositely disposed proximal and distal ends. The proximal end is electrically connected to the electrical signal source and the distal end is electrically connected to the at least one electrode. The electrical lead is for delivering the electrical signal to the at least one electrode. The displacement device is for facilitating application of the first major surface of the at least one electrode to the ocular tissue. The displacement device is securely connected to the electrical lead.

According to another aspect of the present invention, a method is provided for delivering at least one therapeutic agent to an ocular tissue of a subject. One step of the method includes providing an apparatus comprising at least one electrode, a medicament layer including the at least one therapeutic agent, an electrical signal source, and logic configured to control the electrical signal source. The at least one electrode has oppositely disposed, electrically-conductive first and second dome-shaped major surfaces. The medicament layer is disposed on at least a portion of the second major surface. The electrical signal source is electrically connected to the at least one electrode. Next, the electrical signal source is caused to provide a signal having certain characteristics to motivate the at least one therapeutic agent into the ocular tissue.

According to another aspect of the present invention, a method is provided for delivering at least one therapeutic agent to an ocular tissue of a subject. One step of the method includes providing an apparatus comprising at least one electrode, a medicament layer including the at least one therapeutic agent, an electrical signal source, and logic configured to control the electrical signal source. The at least one electrode has oppositely disposed, electrically-conductive first and second dome-shaped major surfaces. The medicament layer is disposed on at least a portion of the second major surface. The electrical signal source is electrically connected to the at least one electrode. Next, at least one of the medicament layer and the at least one electrode is shaped so that delivery of the electrical signal to the at least one electrode motivates the at least one therapeutic agent into the select region of the subject's eye. The electrical signal source is then caused to provide an electrical signal to the at least one electrode to motivate the at least one therapeutic agent into the selection region of the subject's eye.

BRIEF DESCRIPTION OF THE DRAWINGS

The foregoing and other features of the present invention will become apparent to those skilled in the art to which the present invention relates upon reading the following description with reference to the accompanying drawings, in which:

FIG. 4A is a cross-sectional view of the apparatus taken along Line 4A-4A in FIG. 1A;

FIG. 4B is a cross-sectional view of the apparatus taken along Line 4B-4B in FIG. 1B;

FIG. 6 is a perspective view showing a medicament layer being placed onto at least one electrode of the apparatus in FIG. 1A;

FIG. 7 is a perspective view showing the medicament layer disposed on the at least one electrode in FIG. 6;

In FIG. 14, a 1 mL suspension of TA was separated into 8 equal portions of approximately 0.13 mL (5.0 mg TA). The negative control contained no drug. The positive control was taken from the standard concentration used in the calibration curve. Based on the 5.0 mg TA initial sample and the 3 mL B-Cell bottom chamber capacity, the maximum final concentration=1.67 mg/mL. Percent throughput was calculated based on this maximum. Total percent throughput is based on the entire 40 mg present in the vial—17.72 mg, or 44 percent of those 40 mg were detected by UV-Vis;

DETAILED DESCRIPTION

Figure 1:
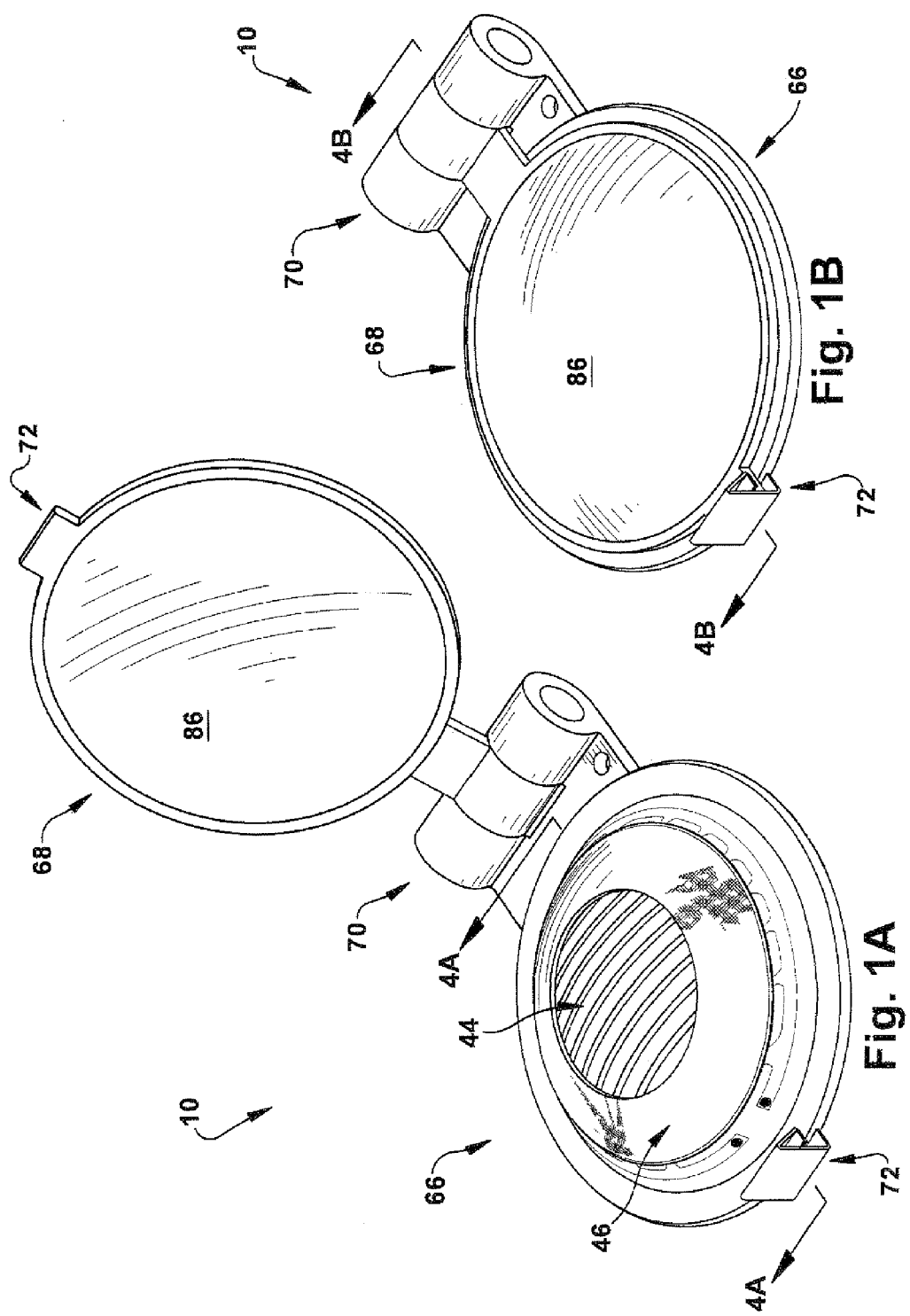
FIG. 1A is a perspective view showing an open configuration of an apparatus for delivering a drug to an ocular tissue constructed in accordance with one aspect of the present invention.
FIG. 1B is a perspective view showing the apparatus of FIG. 1A in a closed configuration.

The present invention relates generally to an apparatus and method for delivering at least one therapeutic agent to an ocular tissue, and more particularly to a dielectrophoretic apparatus and related method for delivering at least one therapeutic agent to an ocular tissue of a subject. As representative of the present invention, FIGS. 1A-B illustrate an apparatus 10 for delivering at least one therapeutic agent to an ocular tissue of a subject. One aspect of the present invention provides a non-invasive apparatus 10 and method 12 (FIG. 5) that takes advantage of the principles of dielectrophoresis to modulate delivery of at least one therapeutic agent to ocular tissue. Unlike conventional therapeutic agent delivery modalities, one aspect of the present invention provides increased patient safety, the ability to deliver both polar and non-polar agents of varying size, programmable dose control, and potentially lower cost of subject care.

Unless otherwise defined, all technical terms used herein have the same meaning as commonly understood by one of ordinary skill in the art to which the present invention pertains.

In the context of the present invention, the term "ocular tissue" can refer to any one or combination of the tissues comprising the eye, such as the sclera, the conjunctiva, the cornea, the eyelid, tissues within the sclera (e.g., the retina) and outside the sclera (e.g., ocular muscles within the orbit), and tissues neurologically connected to (but distinct from) the eye, such as the optic nerve, the geniculate nucleus, and the visual cortex.

As used herein, the term "subject" can refer to any warm-blooded organism including, but not limited to, human beings, pigs, rats, mice, dogs, goats, sheep, horses, monkeys, apes, rabbits, cattle, etc.

As used herein, the terms "therapeutic agent", "drug", "agent", "chemical compound", and "chemical substance" can refer to any polar or non-polar molecule or moiety that is capable of exhibiting a dipole moment when exposed to an electric field. The terms can include, but are not limited to therapeutically effective agents (i.e., agents that are capable of having a biological effect), such as pharmaceutical agents, drugs, or biological agents.

As used herein, the term "medicament layer" can refer to a suitable reservoir for storing and releasing at least one therapeutic agent, either with or without a vehicle.

As used herein, the term "vehicle" can refer to any non-toxic carrier composition suitable for administration of a drug or agent into ocular tissue. Examples of vehicles can include any of the standard pharmaceutical carriers, such as a phosphate buffered saline solution, water, emulsions (e.g., oil/water emulsions), various types of wetting agents, and excipients.

As used herein, the term "signal" can refer to voltage signals and current signals.

As used herein, the term "logic" can refer to hardware, firmware, software and/or combinations thereof to perform a function(s) or an action(s), and/or to cause a function or action from another component. For example, based on a desired application or need, logic may include a software controlled microprocessor, discreet logic, such as an application specific integrated circuit (ASIC), a programmed logic device, memory device containing instructions, or the like. "Logic" may also be fully embodied as software on a computer-readable medium.

As used herein, the term "therapeutically effective amount" can refer to that amount of a therapeutic agent that results in amelioration of symptoms or a prolongation of survival in a subject with an ocular disease or condition. A therapeutically effective amount relieves to some extent one or more symptoms of an ocular disease or condition or returns to normal either partially or completely one or more physiological or biochemical parameters associated with or causative of the ocular disease or condition.

As used herein, the term "anterior segment" can refer to refer to at least one of the cornea, anterior chamber, iris, ciliary body, and lens of the eye.

As used herein, the term "posterior segment" can refer to at least one of the vitreous, posterior chamber, choroid, retina, sclera, and optic nerve of the eye.

One aspect of the present invention includes an apparatus 10 (FIGS. 1A-B) and method 12 (FIG. 5) for delivering at least one therapeutic agent to an ocular tissue of a subject via dielectrophoresis. To date, most devices and methods for delivering therapeutic agents (e.g., drugs) aided by an electromotive force have involved the use of a simple cathode or anode coupled with a drug source and a direct current (DC) electrical signal. The use of a DC electrical signal alone, however, may have certain disadvantages including, but not limited to, the formation of harmful or undesirable chemical byproducts at the cathode or anode. Moreover, such devices and methods are characterized as "iontophoresis" devices and methods since they are primarily limited to effecting transport of ionic or strongly polar compounds. Many compounds (including drugs) may not be polar or ionic and/or may be difficult to ionize, rendering the use of iontophoretic devices and methods ineffective on such compounds.

Regarding polarization, many compounds exhibit no dipole (areas of equal charge separated by a distance) in the absence of an electric field because no free charges exist on any site of the compound or, if present, the charges are randomly distributed such that no net charge exists on the compound. Such compounds may be polarized and achieve a net dipole if they contain sites capable of being acted upon by an applied electric field. Such sites may comprise any distinct chemical group or moiety within a larger compound that is capable of being attracted or repelled by an applied electric field. The sites are termed "nanosites" when their size is less than about 100 nanometers. Such nanosites can include, for example, carbonyl, sulfoxide, nitro, and hydroxide groups.

Unlike iontophoresis, one aspect of the present invention includes a dielectrophoretic apparatus 10 (FIGS. 1A-B) and method 12 (FIG. 5) for motivating any polarizable chemical compound, including compounds that are difficult to polarize, such as non-polar drugs and large molecule compositions. Dielectrophoresis involves providing a non-uniform alternating (AC) or DC electric field to a compound or agent. The non-uniform electric field, in addition to inducing a dipole in the compound or agent, sets up an electrical field gradient that provides an electromotive force on the newly polarized compound or agent, the magnitude and direction of which are dependent on several factors. A more detailed explanation of dielectrophoresis and its operating principles are disclosed in U.S. patent application Ser. No. 11/874,859 (hereinafter, "the '859 application"), the entirety of which is hereby incorporated by reference.

Figure 2:
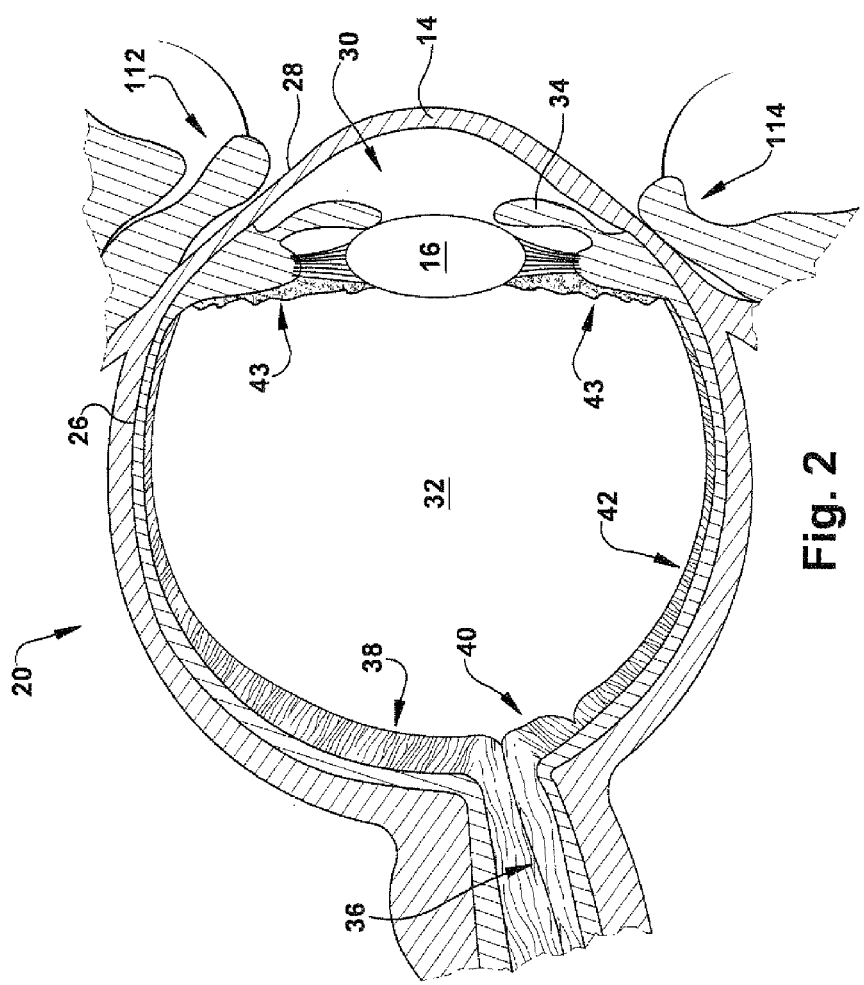
FIG. 2 is a cross-sectional view of a human eye.

One aspect of the present invention includes an apparatus 10 (FIGS. 1A-B) and method 12 (FIG. 5) for delivering at least one therapeutic agent to an ocular tissue of a subject, such as a human eye 20 (FIG. 2). As shown in FIG. 2, about one-sixth of the outer layer of the eye 20 bulges forward as the cornea 22. The cornea 22 is the primary structure focusing light entering the eye 20 (along with the secondary focusing structure, the lens 24). Along its circumference, the cornea 22 is continuous with the sclera 26, which is the white, opaque portion of the eye 20. The sclera 26 provides protection and serves as an attachment for the extraocular muscles (not shown) that move the eye 20. The eye 20 additionally includes the conjunctiva 28, which begins at the outer edge of the cornea 22 and covers the visible part of the sclera 26. The conjunctiva 28 secretes oils and mucous that moisten and lubricate the eye 20. Other portions of the eye 20 include the anterior compartment 30, the posterior compartment 32, the iris 34, the optic nerve 36, the macula lutea 38, the retina 40, the choroid 42, and the pars plana 43.

In one aspect of the present invention, the apparatus 10 (FIGS. 1A-B) comprises at least one electrode 44, a medicament layer 46 including at least one therapeutic agent, an electrical signal source 48 (FIG. 10), and logic configured to control the electrical signal source. The at least one electrode 44 (FIGS. 1A-B) can comprise any one or combination of electrodes capable of providing an electric field to an area sufficient to motivate at least one therapeutic agent into an ocular tissue. To ensure proper transmission of electrical energy, the at least one electrode 44 includes at least two separate, electrically-conductive portions or components that are biased against one another. The at least one electrode 44 can comprise a single electrode or, alternatively, two or more independent, electrically-conductive members separated by an insulator. For example, the at least one electrode 44 can comprise any irregularly-shaped or non-uniform electrode capable of providing a non-uniform electric field to an area sufficient to induce dielectrophoretic transport of at least one therapeutic agent.

The at least one electrode 44 has a flexible, dome-shaped configuration that is contoured to the three-dimensional shape of the ocular tissue (e.g., the eye 20). The at least one electrode 44 includes an electrically-conductive first major surface 50 oppositely disposed from an electrically-conductive second major surface 52 (FIGS. 4A-B). The first major surface 50 is curved such that the first major surface substantially conforms to the contour of the ocular tissue when the first major surface is in contact with the ocular tissue. For example, the first major surface 50 can have a radius of curvature substantially similar to the radius of curvature of the sclera 26 or cornea 22. As described in more detail below, the at least one electrode 44 can be judiciously shaped to facilitate delivery of at least one therapeutic agent to a select region of ocular tissue.

The at least one electrode 44 can be made of any material capable of conducting an electrical current, such as platinum, platinum-iridium, stainless steel, gold-plated copper, or the like. Additionally or optionally, at least a portion of the at least one electrode 44 is embedded within a polymeric material (or other similar material) (e.g., silicone) to protect ocular tissue from abrasion, promote biocompatibility and/or electrical conduction, and facilitate fixing the at least one electrode in place during delivery.

Figure 3A:
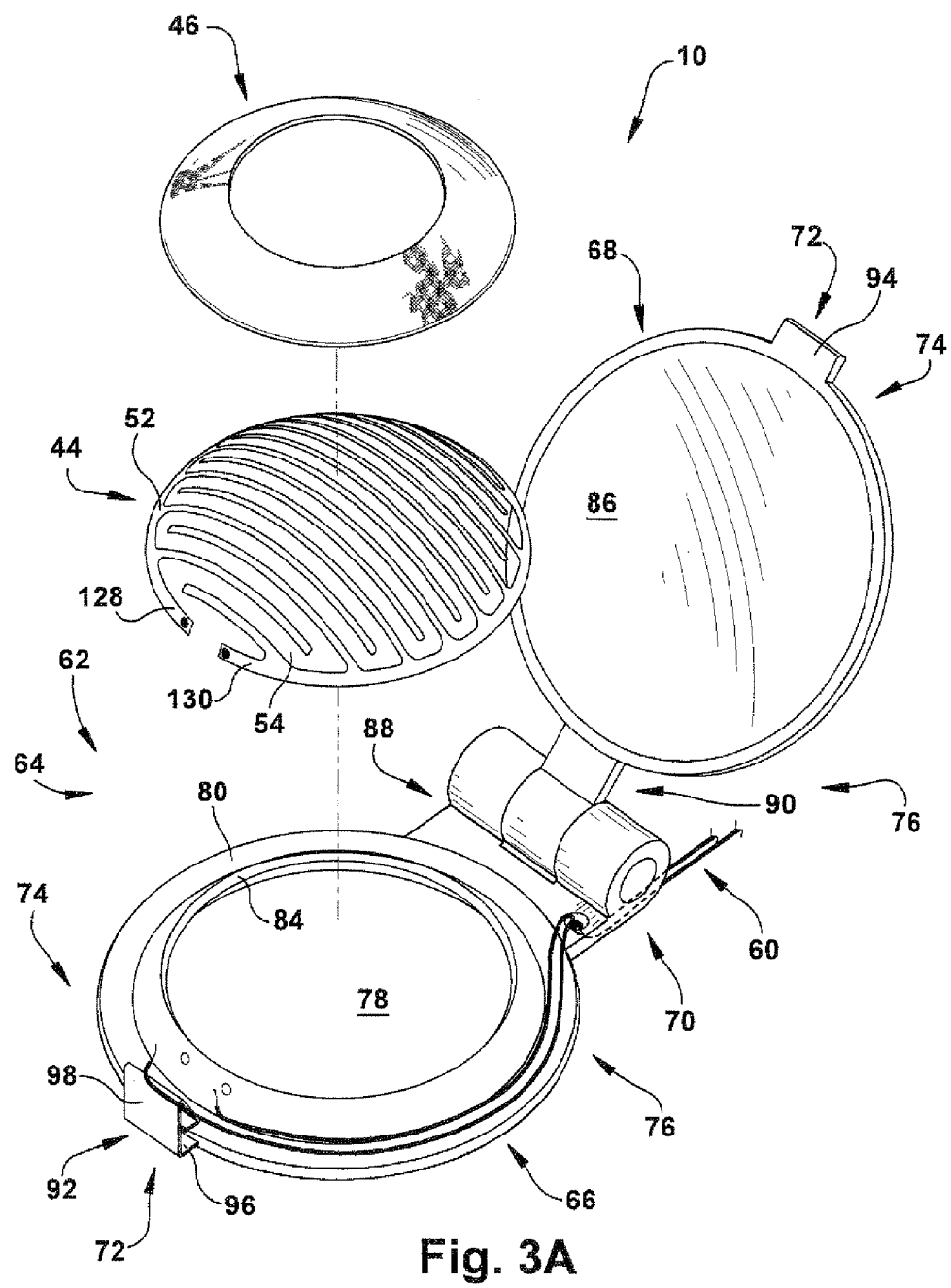
FIG. 3A is an exploded perspective view showing the apparatus in FIG. 1A.
Figure 3B:
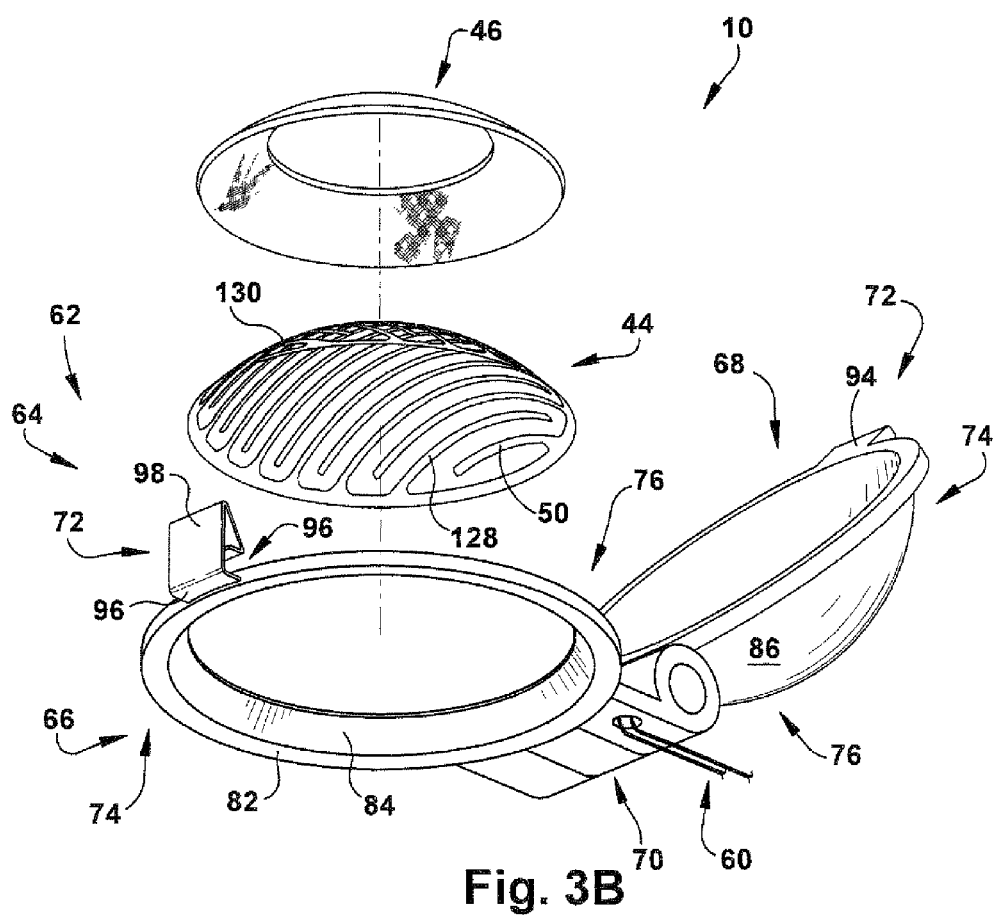
FIG. 3B is a different perspective view showing the apparatus in FIG. 3A.

As one example of the present invention, it will be appreciated that ongoing reference to the at least one electrode 44 shall include an interdigitated electrode. In general, an interdigitated electrode can include any set of at least two electrodes that contain interwoven projections. As shown in FIGS. 3A-B, the at least one electrode 44 (e.g., an interdigitated electrode) is comprised of a first electrically-conductive member 128 that is separated by an insulator from a second electrically-conductive member 130. Each of the first and second electrically-conductive members 128 and 130 comprise a "comb" electrode (i.e., an electrode having a number of relatively long, flat prongs that are evenly spaced) whose prongs are interleaved with one another. The at least one electrode 44 (e.g., an interdigitated electrode) can additionally include at least one passage 54 sufficient to allow at least one therapeutic agent to pass therethrough. The at least one electrode 44 (e.g., an interdigitated electrode) can have a material composition and dimensions that allow for substantial flexibility and conformability to ocular tissue. As noted above, the first and second electrically-conductive members 128 and 130 comprising the at least one electrode 44 (e.g., an interdigitated electrode) may be spaced apart by an insulator (not shown) made of any insulating material suitable for use in designing an arrangement of electrodes and/or circuits (e.g., fiberglass or TEFLON). More specific details concerning the design and function of interdigitated electrodes are disclosed in the '859 application.

As shown in FIG. 1A, the medicament layer 46 is disposed on at least a portion the second major surface 52 (FIGS. 3A-B) of the at least one electrode 44 (e.g., an interdigitated electrode). The medicament layer 46 can be shaped to preferentially deliver the at least one therapeutic agent to a select region of ocular tissue. The ring-shaped medicament layer 46 shown in FIGS. 3A-B, for example, can facilitate selective delivery of at least one therapeutic agent to the sclera 26 of the eye 20 while also avoiding or mitigating delivery of the at least one therapeutic agent to the cornea 22. It will thus be appreciated that the medicament layer 46 can have any size and shape, depending upon the particular application of the present invention.

The medicament layer 46 can comprise a matrix formed from a sponge, gel (e.g., hydro-gel), viscous liquid, or the like. The medicament layer 46 can be applied to the second major surface 52 of the at least one electrode 44 (e.g., an interdigitated electrode) by spraying, coating or placing. The material(s) used to form the medicament layer 46 can include any one or combination of materials capable of storing and releasing the at least one therapeutic agent and, optionally, at least one vehicle. For example, the medicament layer 46 can be comprised of a biocompatible, non-biodegradable polymeric material made from a homopolymer, a copolymer, straight polymers, branched polymers, cross-linked polymers, stimuli-responsive polymers, or a combination thereof. Examples of such polymers can include silicone, polyvinyl alcohol, ethylene vinyl acetate, polylactic acid, nylon, polypropylene, polycarbonate, cellulose, cellulose acetate, polyglycolic acid, polylactic-glycolic acid, cellulose esters, polyethersulfone, acrylics, their derivatives, and combinations thereof. It should be appreciated that the medicament layer 46 may also be disposed on the first major surface 50 of the at least one electrode 44 (e.g., an interdigitated electrode) or at least partially embedded therein.

The medicament layer 46 can include any one or combination of polar and/or non-polar therapeutic agents. For example, the medicament layer 46 can include such ophthalmic medications as anti-infectives, antibiotics, anti-inflammatory agents (e.g., triamcinolone), non-steroidal anti-inflammatory agents, anti-fungal agents, glaucoma medications (e.g., alpha-2 agonists, beta blockers, carbonic anhydrase inhibitors, miotics, prostaglandin agonists, and sympathomimetics), mast cell stabilizers, anti-proliferative agents, steroids, corticosteroids, hormones, small molecules, cytokines, growth factors, antibodies or antibody fragments, immune system modulators, vectors, polynucleotides, nucleic acids, RNAs, miRNAs, siRNAs, DNAs, aptamers, carbohydrates, recombinant or native peptides, polypeptides and proteins (e.g., TIMP-3), enzymes, enzyme inhibitors, and combinations thereof. More specific examples of such therapeutic agents, as well as others are known in the art.

It will be appreciated that the apparatus 10 can include more than one medicament layer 46, and that each medicament layer can contain the same or different type of therapeutic agent. Additionally, it will be appreciated that a single medicament layer 46 can include two or more compartments (not shown), each of which is also made from a gel, viscous liquid, etc. If appropriate, mixtures of therapeutic agents can be stored in a common compartment while other single therapeutic agents (or mixtures) are stored in one or more separate compartments. The release characteristics of the respective compartments can be adjusted according to specific applications of the present invention.

Figure 10:
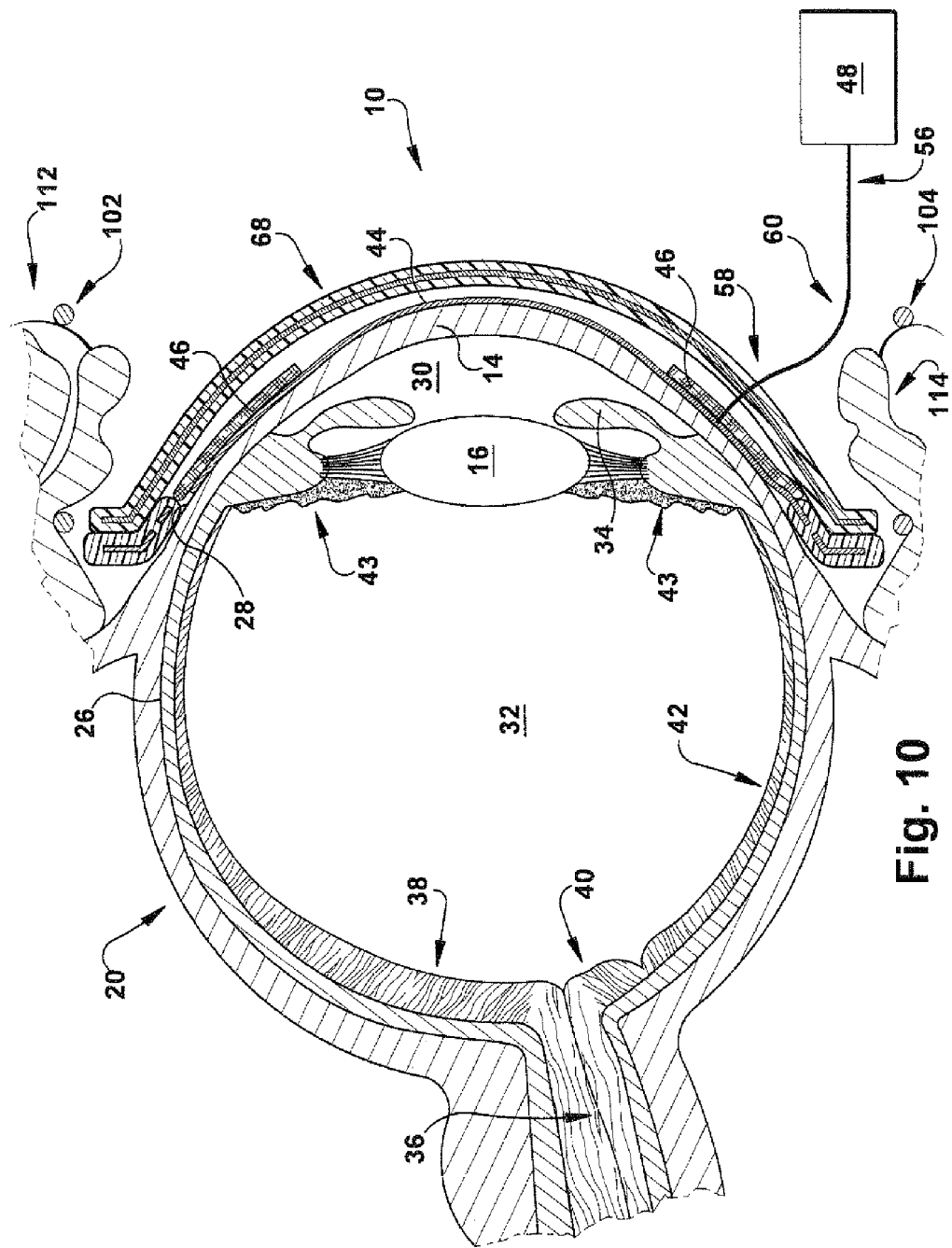
FIG. 10 is a cross-sectional view taken along Line 10-10 in FIG. 9 showing the apparatus of FIG. 9 placed over the human eye.

The apparatus 10 additionally comprises an electrical signal source 48 (FIG. 10) for providing an electrical signal to the at least one electrode 44 (e.g., an interdigitated electrode). The electrical signal source 48 is capable of providing an AC signal, a DC signal, or a combination thereof. The electrical signal source 48 can be electrically connected to the at least one electrode 44 (e.g., an interdigitated electrode) via a direct electrical link or a wireless link (e.g., an RF link). As shown in FIG. 10, for example, proximal and distal ends 56 and 58 of an electrical lead 90 can be electrically connected to the electrical signal source 48 and the at least one electrode 44 (e.g., an interdigitated electrode), respectively.

In one example of the present invention, the electrical signal source 48 provides an electrical signal having certain characteristics. The certain characteristics can comprise at least one orienting frequency to orient the at least one therapeutic agent, and at least one motivating frequency sufficient to motivate the at least one therapeutic agent into the ocular tissue. For example, the at least one orienting frequency can comprise an AC signal having a relatively low frequency, and the motivating frequency can comprise an AC signal having a relatively high frequency. Alternatively, the at least one orienting frequency can comprise an AC signal delivered from an AC signal source, and the at least one motivating frequency can comprise a DC signal delivered from a DC signal source. Other examples of electrical signals having certain characteristics are disclosed in the '859 application and described below.

The apparatus 10 additionally includes logic configured to control the electrical signal source 48. The logic may be configured to monitor and record current and phase data from the at least one electrode 44 (e.g., an interdigitated electrode) and to calculate dielectric information regarding the at least one therapeutic agent as a function of the electrical signal frequency. Dielectric information may include, but is not limited to, capacitance, conductance, permittivity ($\in'$), dielectric loss factor ($\in''$), and impedance information. Dielectric information may be plotted or stored as a function of electrical signal frequency to facilitate selection of appropriate operating frequencies that allow for the at least one therapeutic agent to be motivated into ocular tissue. More specific details concerning the logic used to modulate the electrical signal are disclosed in the '859 application.

Referring to FIGS. 3A-B, the apparatus 10 also includes a positioning member 62 for placing at least a portion of the first major surface 50 of the at least one electrode 44 (e.g., an interdigitated electrode) into contact with an ocular tissue. The positioning member 62 can be attached to the at least one electrode 44 (e.g., an interdigitated electrode) at one or more points and/or at least partially envelop the at least one electrode 44 (e.g., an interdigitated electrode). Moreover, the positioning member 62 can have any desired shape and size sufficient to facilitate placement of the at least one electrode 44 (e.g., an interdigitated electrode). The positioning member 62 can be made of an electrically-insulative material (e.g., plastic, silicone, etc.), and can have a rigid, semi-rigid, or flexible configuration.

In one example of the present invention, the positioning member 62 can comprise a clam-shaped housing 64. As shown in FIGS. 3A-B, the housing 64 comprises a first opposable member 66, a second opposable member 68, a hinge mechanism 70 that operably connects the first and second opposable members, and a securing mechanism 72 for mating the first and second opposable members. The housing 64 can have a rigid or semi-rigid configuration. Additionally, all or only a portion of the housing 64 can be made from an electrically-insulative material, such as silicone or hardened plastic.

As shown in FIGS. 3A-B, the first opposable member 66 is ring-shaped and includes oppositely disposed first and second end portions 74 and 76. The first opposable member 66 includes a central opening 78 that extends between an upper surface 80 and a lower surface 82. The central opening 78 is adapted to receive the at least one electrode 44 (e.g., an interdigitated electrode). The at least one electrode 44 (e.g., an interdigitated electrode) can be securely seated within the central opening 78 of the first opposable member 66 using an adhesive or, alternatively, by integrating the periphery of the first major surface 50 into an inner surface 84 of the first opposable member. It will be appreciated that other means can be used to securely seat the at least one electrode 44 (e.g., an interdigitated electrode) in the central opening 78. For example, the inner surface 84 of the first opposable member 66 can include a ridge or ledge (not shown) upon which the periphery of the first major surface 50 can be securely seated.

The second opposable member 68 has a configuration similar to the configuration of the first opposable member 66. As shown in FIGS. 3A-B, for example, the second opposable member 68 is ring-shaped and includes oppositely disposed first and second end portions 74 and 76. The second opposable member 68 also includes a central opening 78 that extends between an upper surface 80 and a lower surface 82. A dome-shaped member 86 is securely seated within the central opening 78 of the second opposable member 68. The dome-shaped member 86 is configured to cover the second major surface 52 of the at least one electrode 44 (e.g., an interdigitated electrode) and the medicament layer 46 when the first and second opposable members 66 and 68 are securely mated together. The dome-shaped member 86 can be made of a rigid or semi-rigid material (e.g., a hardened plastic), and can be secured within the central opening 78 of the second opposable member 68 using an adhesive, for example, or any other suitable means. It should be appreciated that the dome-shaped member 86 can be a continuous, integral part of the second opposable member 68.

The hinge mechanism 70 of the housing 64 provides a means for selectively mating the first and second opposable members 66 and 68. As shown in FIGS. 3A-B, the hinge mechanism 70 is integrally formed with the second end portion 76 of each of the first and second opposable members 66 and 68. The hinge mechanism 70 can have a known hinge configuration, such as a strap hinge, butt hinge, or back flap hinge. As shown in FIGS. 3A-B, for example, the hinge mechanism 70 can comprise a female portion 88 integrally formed with the second end portion 76 of the first opposable member 66, and a male portion 90 integrally formed with the second end portion of the second opposable member 68. It will be appreciated that the hinge mechanism 70 can have a configuration other than the one shown in FIGS. 3A-B. For example, the hinge mechanism 70 can have a one-piece configuration (not shown) comprising a single piece of material (e.g., a U-shaped piece of flexible plastic) that flexibly connects the second end portion 76 of the first opposable member 66 with the second end portion of the second opposable member 68.

The housing 64 additionally comprises a securing mechanism 72 for mating the first opposable member 66 with the second opposable member 68. The securing mechanism 72 comprises a male member 92 integrally formed with the first end portion 74 of the first opposable member 66, and female member 94 integrally formed with the first end portion of the second opposable member 68. The male member 92 comprises a base portion 96 that is securely mated with an insertion tab 98. The female member 94 comprises tab-shaped member mating with the base portion 96 of the male member 92. It will be appreciated that the securing mechanism 72 can be located elsewhere about the housing 64, and that the securing mechanism can have a configuration other than the one shown in FIGS. 3A-B.

Figure 5:
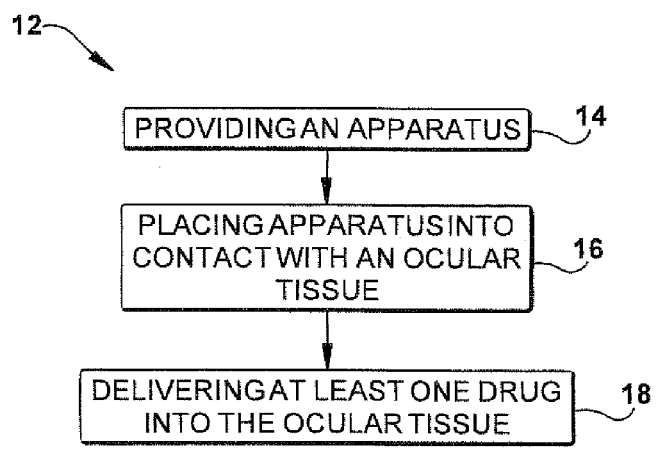
FIG. 5 is a process flow diagram illustrating a method for delivering a drug to an ocular tissue of subject according to another aspect of the present invention.

FIG. 5 is a process flow diagram illustrating another aspect of the present invention. In FIG. 5, a method 12 is provided for delivering at least one therapeutic agent to an ocular tissue of a subject. The method 12 includes providing an apparatus 10 at Step 14. The apparatus 10 can be identically or similarly constructed as the apparatus shown in FIGS. 1A-B. For example, the apparatus 10 can comprise at least one electrode 44 (e.g., an interdigitated electrode), a medicament layer 46 including at least one therapeutic agent, an electrical signal source 48, and logic configured to control the electrical signal source.

At Step 16, at least a portion of the apparatus 10 is placed into contact with the ocular tissue of the subject. The placement location, type of therapeutic agent (or agents) comprising the medicament layer 46, and the size and shape of the medicament layer will depend on the subject's anatomy, the age of the subject, the presence or absence of an ocular condition or disease, as well as other factors. To treat retinal inflammation, for example, the medicament layer 46 can include a desired concentration of triamcinolone. Alternatively, in a subject with advanced macular degeneration, the medicament layer 46 can include a desired concentration of ranibizumab or TIMP-3.

Prior to contacting the apparatus 10 with the ocular tissue, the medicament layer 46 can be shaped to optimize delivery of the therapeutic agent(s) to the ocular tissue. In a subject suffering from posterior segment eye disease, for example, the medicament layer 46 can be shaped as shown in FIGS. 3A-B to optimize delivery of the therapeutic agent(s) through the pars plana 43 and into at least one tissue comprising the posterior segment of the eye 20. Alternatively, in a subject suffering from corneal inflammation, the medicament layer 46 can have a circular or oval-shaped configuration (FIG. 11) and be placed on or near the center of the at least one electrode 44 (e.g., an interdigitated electrode) adjacent the corneal surface 14 to facilitate delivery of the therapeutic agent(s) into the inflamed corneal tissue.

If it has not been done so already, the medicament layer 46 is placed into contact with the second major surface 52 of the at least one electrode 44 (e.g., an interdigitated electrode) (FIGS. 6-7) by first depressing the insertion tab 98 of the securing mechanism 72 so that the second opposable member 68 is freed from the first opposable member 66. Next, the first and second opposable members 66 and 68 are separated (e.g., pulled apart using tactile force) so that the housing 64 obtains an opened configuration (FIG. 6). In the opened configuration, the medicament layer 46 can be placed into contact with the second major surface 52 of the at least one electrode 44 (e.g., an interdigitated electrode) (FIG. 7). After the medicament layer 46 is securely disposed on the second major surface 52, the second opposable member 68 is urged toward the first opposable member 66 (e.g., using tactile force) until the insertion tab 98 is received by the channel and the first and second opposable members are securely mated with one another.

Figure 8:
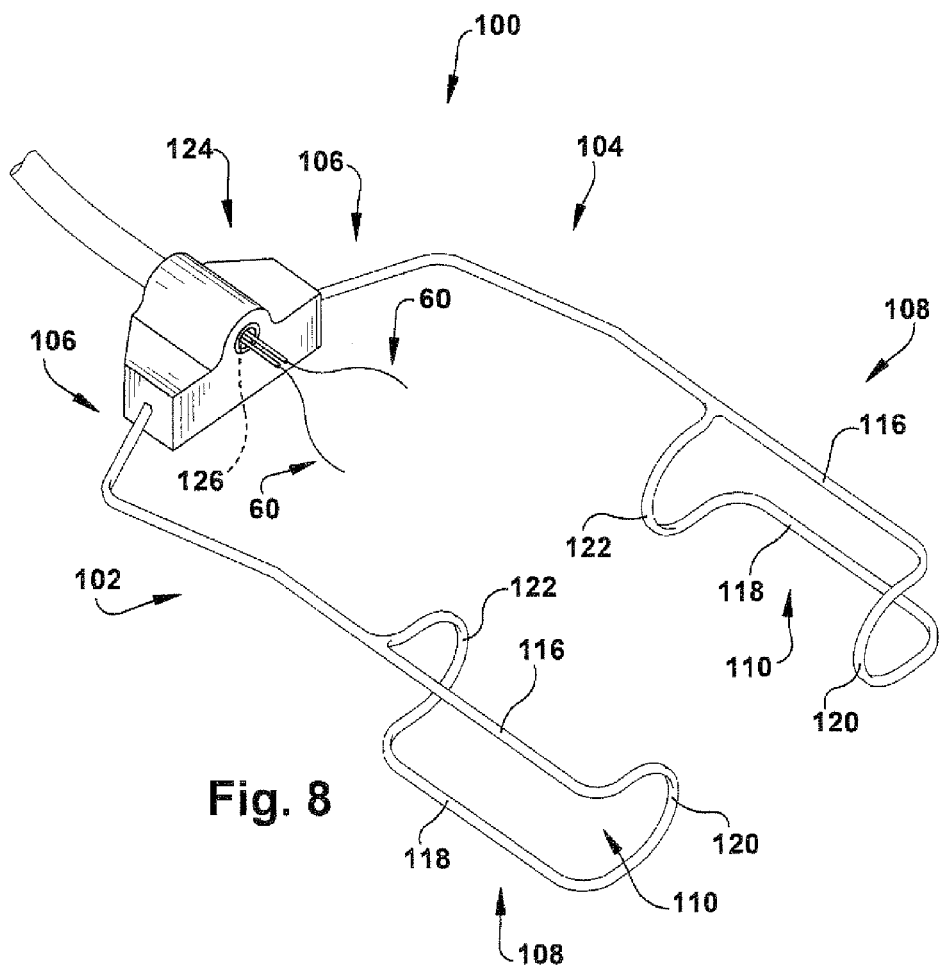
FIG. 8 is a perspective view showing a displacement device constructed in accordance with another aspect of the present invention.

Next, a displacement device 100 (FIG. 8) is used to place the apparatus 10 into contact with the ocular tissue. As shown in FIG. 8, the displacement device 100 comprises a lid speculum having oppositely disposed first and second arm members 102 and 104. Each of the first and second arm members 102 and 104 has a flexible, wire-like configuration and includes proximal and distal end portions 106 and 108. The first and second arm members 102 and 104 can be separate segments or, alternatively, be integrally formed with one another (e.g., at the proximal end portion) in a U-shaped configuration. The first and second arm members 102 and 104 can be made from any one or combination of biocompatible materials, such as titanium, stainless steel, or hardened plastic.

The distal end portion 108 of each of the first and second arm members 102 and 104 includes a channel 110 for receiving at least a portion of an upper eyelid 112 and a lower eyelid 114 (respectively). Each of the channels 110 is comprised of oppositely disposed first and second major segments 116 and 118 joined together by annular-shaped first and second minor segments 120 and 122. It will be appreciated that each of the channels 110 can have a configuration other than the one shown in FIG. 8. For example, each of the channels 110 can be formed from a semi-cylindrical piece of solid material (e.g., plastic).

The displacement device 100 further comprises a connection member 124 that operably joins the first and second arm members 102 and 104, as well as the electrical lead 60. The connecting member 124 can have a wedge-shaped configuration and be comprised of rigid or semi-rigid material, such as rubber. The connecting member 124 includes a first channel (not shown in detail) for receiving the first and second arm members 102 and 104, and a second channel 126 for receiving the electrical lead 60. It will be appreciated that the connecting member 124 can have any other configuration suitable for joining the first and second arm members 102 and 104 and the electrical lead 60.

Figure 9:
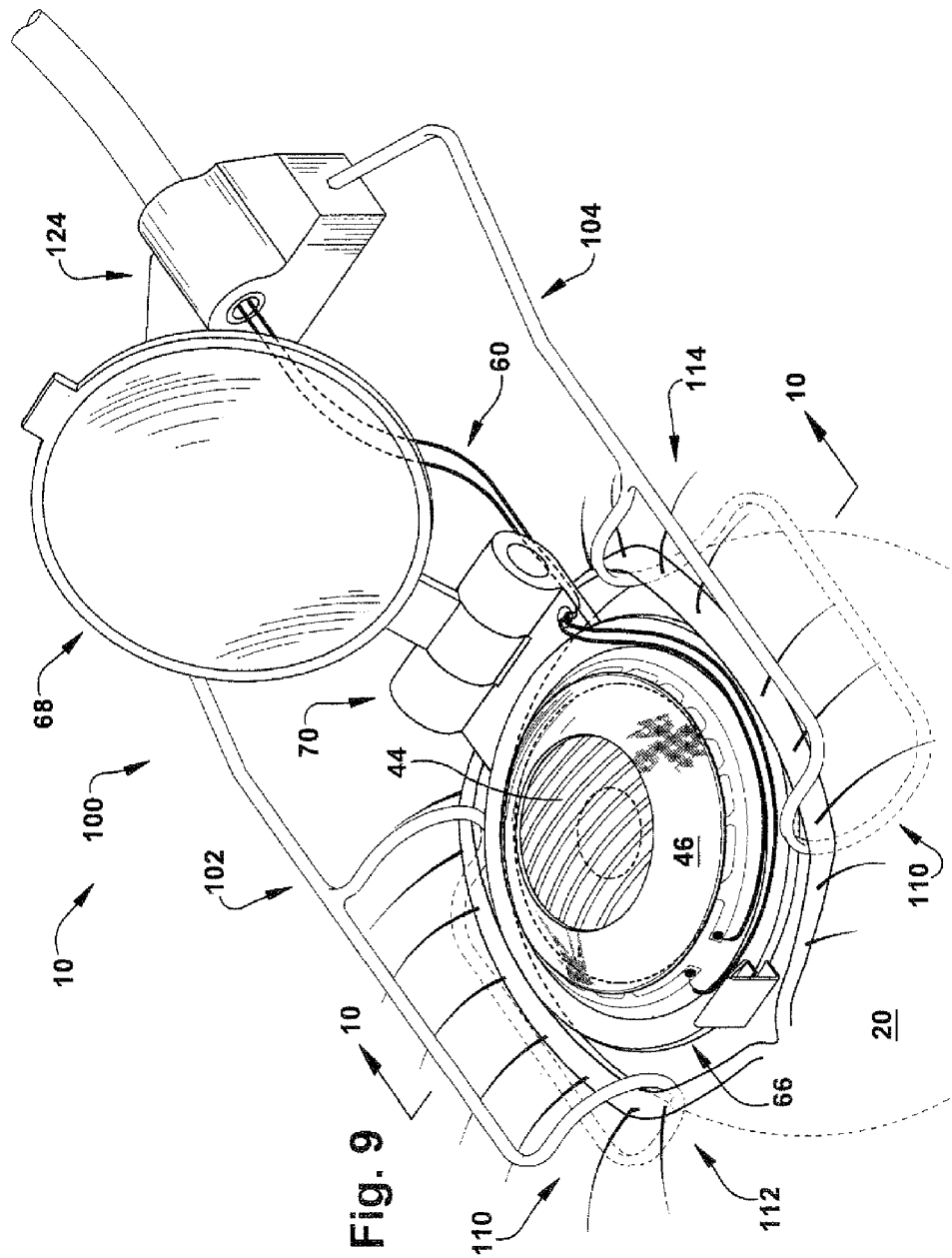
FIG. 9 is a perspective view showing the apparatus in FIG. 1A placed over a human eye using the displacement device in FIG. 8.

If it has not been done so already, the electrical signal source 48 can next be electrically connected to the at least one electrode 44 (e.g., an interdigitated electrode) (FIG. 10). After doing so, the displacement device 100 is positioned substantially adjacent the eye 20. As the displacement device 100 is moved into position over the eye 20, the first and second arm members 102 and 104 can be moved towards one another using tactile force. The distal end portion 108 of each of the first and second arm members 102 and 104 can then be positioned about the upper and lower eyelids 112 and 114 so that the channel 110 of each of the first and second arm members engages at least a portion of the upper and lower eyelids (respectively). As shown in FIG. 9, the first and second arm members 102 and 104 can then be released so that the upper and lower eyelids 112 and 114 are displaced and the surface of the subject's eye 20 is exposed.

After displacing the upper and lower eyelids 112 and 114, the apparatus 10 is positioned adjacent the subject's eye 20 so that the curvature of the first major surface 50 substantially conforms to the contour of the eye's surface (FIG. 10). It will be appreciated that the curvature of the first major surface 50 and the curvature of the subject's eye 20 can be determined prior to placing the apparatus 10 to ensure a snug fit between the first major surface and the eye's surface. Additionally, it will be appreciated that the apparatus 10 can be placed at other positions (e.g., over the subject's eyelids 112 and 114) to deliver the therapeutic agent(s) to the ocular tissue.

At Step 18, the at least one therapeutic agent is motivated or delivered into the ocular tissue by causing the electrical signal source 48 to provide an electrical to the at least one electrode 44 (e.g., an interdigitated electrode). In one example of the method 12, the electrical signal source 48 can be activated to send an AC signal having certain characteristics to the at least one 44 (e.g., an interdigitated electrode). The electrical signal source 48 can be activated to cycle through at least one decade of frequencies ranging from about 0.1 Hz to about 20,000 Hz. For example, an AC signal can have an orienting frequency of about 0.1 Hz to about 100 Hz, a motivating frequency of between about 100 Hz and about 20,000 Hz, and an amplitude of between about 1 V to about 10 V. Additionally, an AC signal can be applied for between about 1 minute and about 30 minutes. A more specific description of the electrical signal and the logic used to modulate the electrical signal is disclosed in the '859 application.

Figure 11:
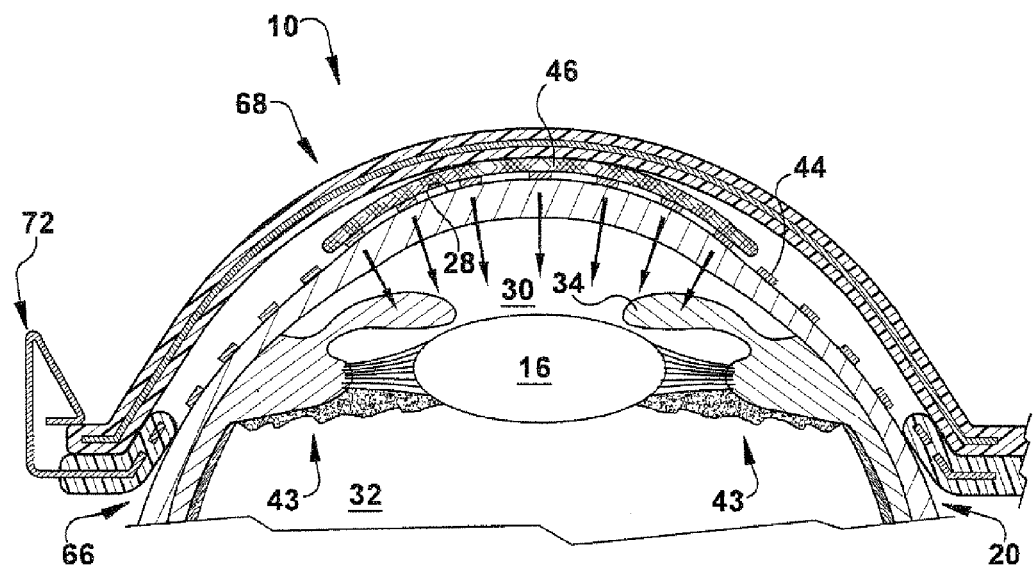
FIG. 11 is a cross-sectional view showing the apparatus in FIG. 10 delivering a drug (arrows) to an anterior segment of the human eye.
Figure 12:
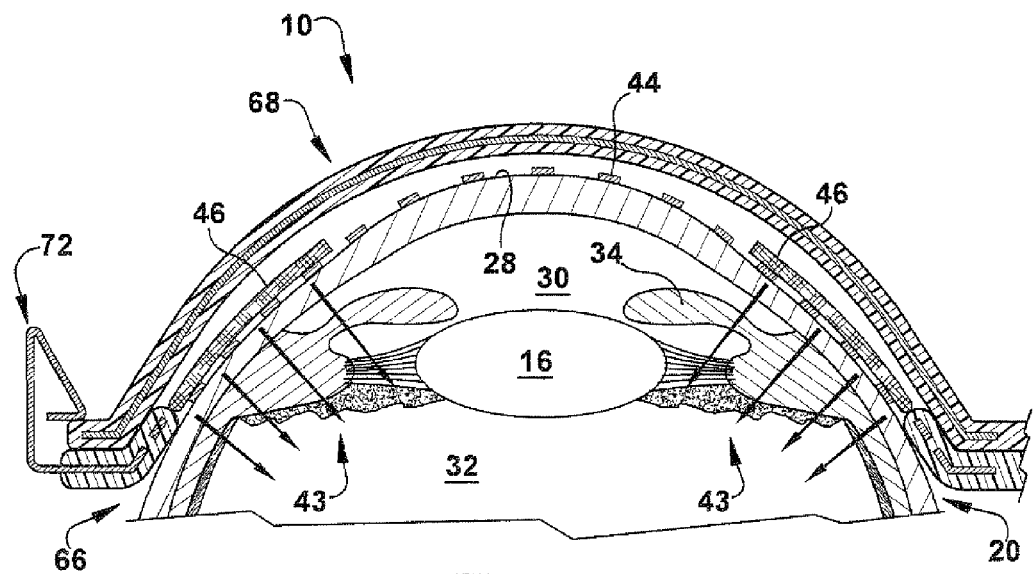
FIG. 12 is a cross-sectional view showing the apparatus in FIG. 10 delivering a drug (arrows) to a posterior segment of the human eye.

Application of the electrical signal motivates the at least one therapeutic agent into the ocular tissue. As shown in FIGS. 11-12, for example, application of an AC signal to the at least one electrode 44 (e.g., an interdigitated electrode) provides a non-uniform electric field, thereby inducing a dipole on the at least one therapeutic agent(s). This, in turn, sets up an electrical field gradient that provides an electromotive force on the newly polarized agent(s) to drive the agent(s) into the subject's eye 20. By modifying the electrical signal (i.e., the frequency, voltage, and time of application), the logic, the apparatus 10 (e.g., the at least one electrode 44 or the medicament layer 46), or a combination thereof, the therapeutic agent(s) can be selectively delivered to a desired portion of the ocular tissue, e.g., an anterior compartment 30 (FIG. 11) or a posterior compartment 32 (FIG. 12) of the subject's eye 20.

It will be appreciated that the method 12 of the present invention can be used to deliver a therapeutically effective amount of the at least one therapeutic agent to ocular tissue and thereby treat a variety of ocular diseases or conditions. Examples of ocular conditions or diseases that may be treated according to the method can include, but are not limited to, macular edema, age-related macular degeneration, anterior, intermediate and posterior uveitis, HSV retinitis, diabetic retinopathy, bacterial, fungal or viral endophthalmitis, eye cancers, glioblastomas, glaucoma, glaucomatous degradation of the optic nerve, and combinations thereof.

The present invention is further illustrated by the following examples, which are not intended to limit the scope of potential applications of the present invention.

Example 1

Background

Nanodielectrophoresis is a method of drug delivery that uses AC to deliver drugs to target tissues. It offers several advantages over implant devices and intravitreal injections, such as increased patient safety, the ability to deliver both small and large compounds, programmable dose control, and potentially lower cost of care. Two in vitro models of drug delivery were used for validity studies. Ranibizumab (48 kd) and triamcinolone acetonide (435 kd) were used for all studies.

Methods

Full thickness rabbit tissue (conjunctiva to retina) was mounted on the surface of an inter-digitated electrode. The test compound (triamcinolone) was placed on the surface of the tissue and the AC electrical field was activated. One millivolt of electricity was applied at various frequencies (Table 1).

An inter-digitated electrode was placed on a full thickness rabbit tissue section (conjunctiva to retina). The test compounds (triamcinolone and ranibizumab) were placed on the surface of the tissue and the AC electrical field was activated. 3 cc of medium was placed underneath the tissue to simulate vitreous. Various frequencies, voltages, and time periods were tested (Table 1). The solution below the tissue was sampled for analysis.

Results

Figure 13:
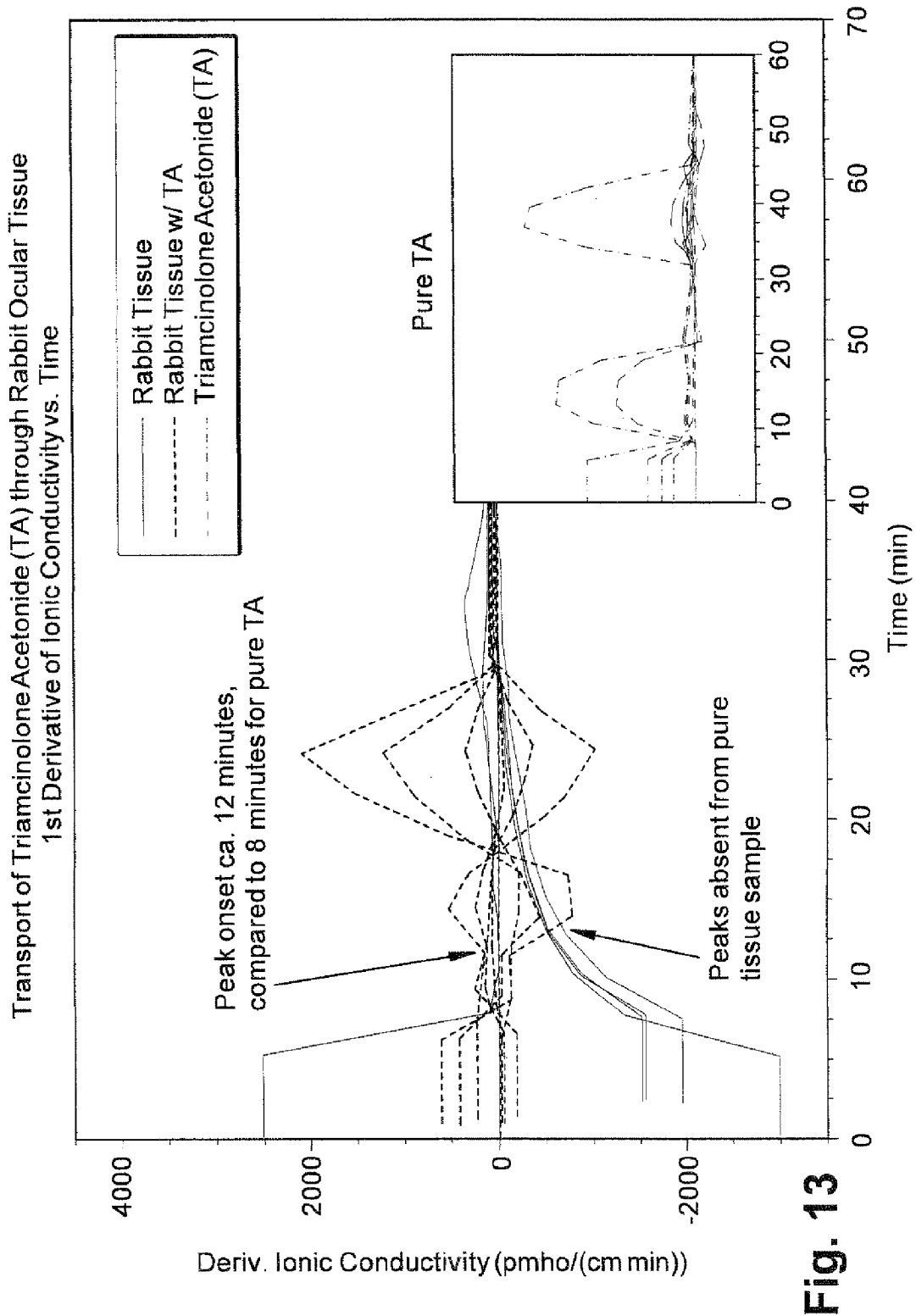
FIG. 13 is a graph comparing ionic conductivity of triamcinolone acetonide (TA) through rabbit ocular tissue over time.

Studies using triamcinolone yielded concentrations ranging from 0.280-0.970 mg/ml depending on the voltage, frequency, and time applied. The clinical dose of triamcinolone is 0.975 mg/ml (4 mg/4 ml vitreous+0.1 cc injection). In as little as 6.7 minutes, clinically efficacious doses could be reached in the preclinical system (FIG. 13).

Studies using ranibizumab, yielded concentrations of 0.070-0.171 mg/ml depending on the voltage, frequency, and time applied. The clinical dose of ranibizumab is 0.123 mg/ml (0.5 mg/4 ml vitreous+0.05 cc injection). In as little as 6.7 minutes, 92.8% throughput could be achieved (FIG. 13).

TABLE 1

Experimental Results

| Study | Concentration (mg/mL) | % Throughput | Absorbance at 250 nm | Voltage (mV) | Low Freq. (Hz) | High Freq. (Hz) | Time (min) |
|---|---|---|---|---|---|---|---|
| Experimental Results of Kenalog in B-cell | | | | | | | |
| 1 | 0.996 | 59.6 | 3.84 | 4 | 10 | 1000 | 15 |
| 2 | 0.639 | 38.3 | 2.48 | 1 | 10 | 1000 | 15 |
| 3 | 0.846 | 50.7 | 3.27 | 1 | 100 | 1000 | 6.7 |
| 4 | 0.280 | 16.8 | 1.12 | 4 | 10 | 1000 | 6.7 |
| 5 | 0.796 | 47.7 | 3.08 | 1 | 10 | 1000 | 6.7 |
| 6 | 0.970 | 58.1 | 3.74 | 1 | 100 | 1000 | 15 |
| 7 | 0.792 | 47.4 | 3.06 | 4 | 100 | 1000 | 15 |
| 8 | 0.587 | 35.2 | 2.29 | 4 | 100 | 1000 | 6.7 |
| Experimental Results of Lucentis in B-cell | | | | | | | |
| 1 | 0.070 | 42.1 | 0.719 | 4 | 10 | 1000 | 15 |
| 2 | 0.123 | 73.7 | 1.259 | 1 | 10 | 1000 | 15 |
| 3 | 0.155 | 92.8 | 1.585 | 1 | 100 | 1000 | 6.7 |
| 4 | 0.113 | 67.8 | 1.158 | 4 | 10 | 1000 | 6.7 |
| 5 | 0.168 | 100.8 | 1.721 | 1 | 10 | 1000 | 6.7 |
| 6 | 0.139 | 83.6 | 1.427 | 1 | 100 | 1000 | 15 |
| 7 | 0.129 | 77.1 | 1.317 | 4 | 100 | 1000 | 15 |
| 8 | 0.171 | 102.5 | 1.750 | 4 | 100 | 1000 | 6.7 |
| Pos. Cont. | 0.129 | 77.1 | 1.317 | 4 | 100 | 1000 | 15 |
| Neg. Cont. | No peaks | — | — | 4 | 100 | 1000 | 15 |

Example 2

Concentration Calibration for Triamcinolone Acetonide

Figure 14:
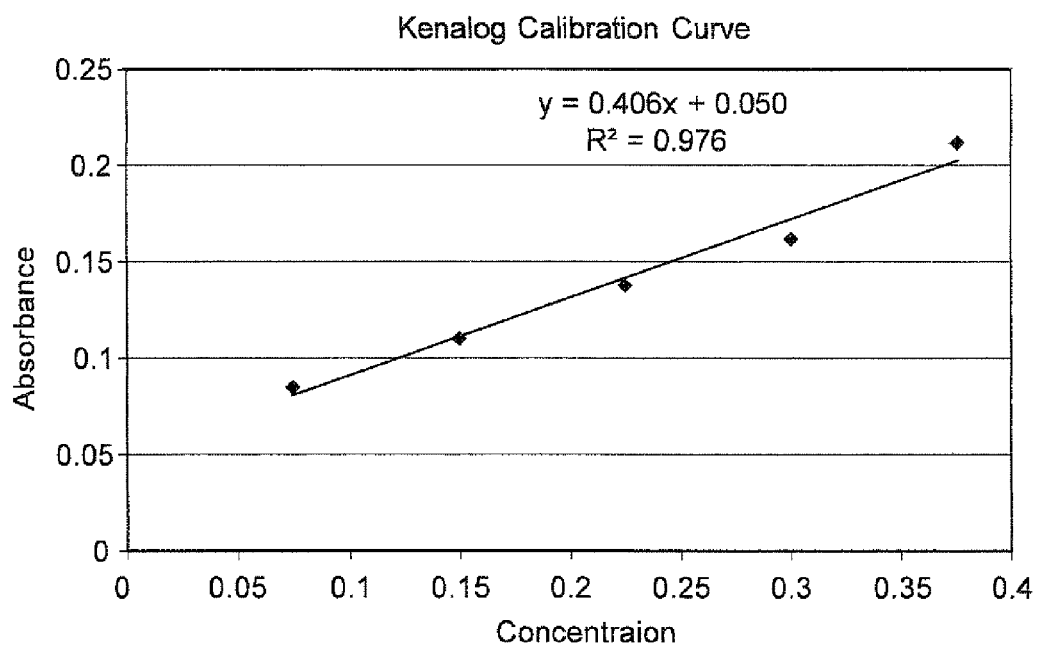
FIG. 14 is a calibration curve for TA.

FIG. 14 illustrates the concentration calibration curve for experiments involving triamcinolone acetonide. Tables 2 and 3 illustrate the particular experimental parameters. Table 4 illustrates correlations of concentrations and different parameters.

TABLE 2

| | Wavelength | Absorbance | Concentration (mg/mL suspension) | Concentration (mg/mL TA) |
|---|---|---|---|---|
| C0 | 238.9 | 0.519 | 1 | 0.375 |
| | 240 | 0.212 | | |
| C1 | 237.1 | 0.162 | 0.8 | 0.3 |
| C2 | 238 | 0.138 | 0.6 | 0.225 |
| C3 | 238.9 | 0.131 | 0.4 | 0.15 |
| | 240 | 0.09 | | |
| C4 | 235 | 0.087 | 0.2 | 0.075 |
| | 243 | 0.084 | | |

TABLE 3

Concentration vs. Absorbance

| 1 | 0.212 | 0.375 |
|---|---|---|
| 0.8 | 0.162 | 0.3 |
| 0.6 | 0.138 | 0.225 |
| 0.4 | 0.1105 | 0.15 |
| 0.2 | 0.0855 | 0.075 |

TABLE 4

| Parameter | Correlation |
|---|---|
| Voltage | −0.34212 |
| Frequency | 0.277 |
| Time | 0.5083 |

Example 3

Lucentis Drug Transport

Figure 15A:
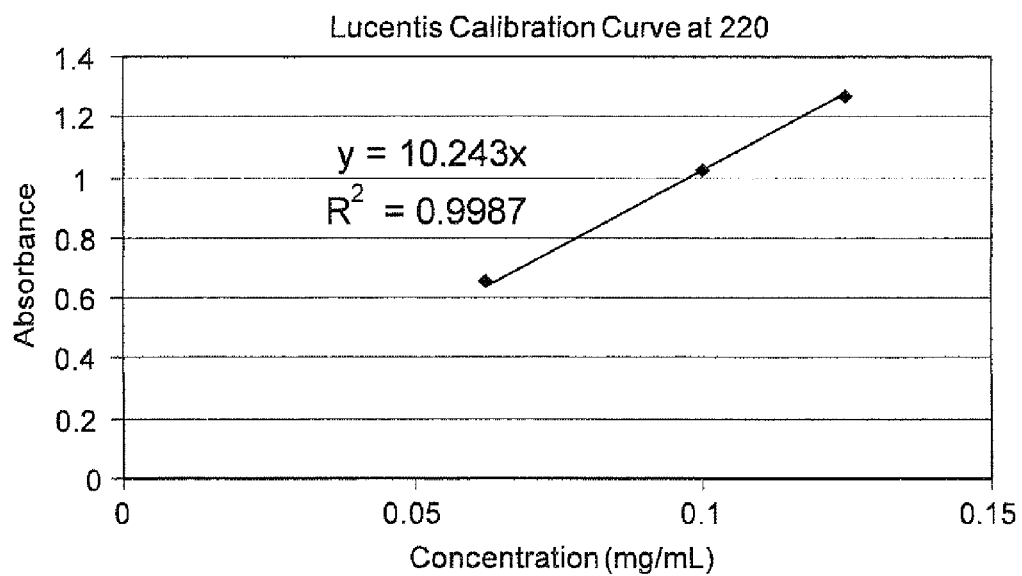
FIG. 15A is a concentration curve for ranibizumab at 220 nm absorbance.
Figure 15B:
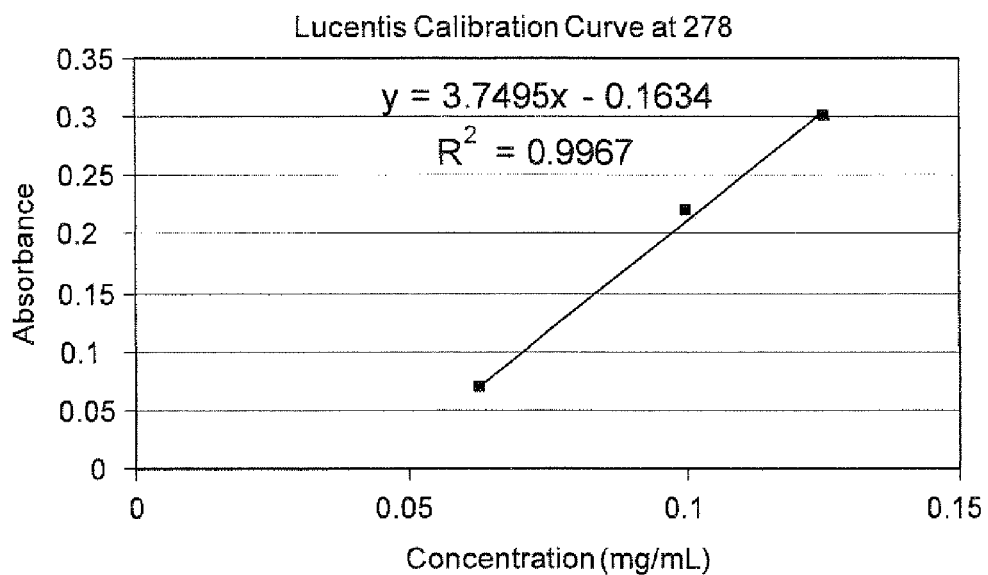
FIG. 15B is a concentration curve for ranibizumab at 278 nm absorbance.

Lucentis was found to have two UV-Vis absorbance peaks, one at 278 nm (±10 nm) and one at 220 nm (±10 nm). Calibration curves and sample readings were generated for both peaks and 220 nm yielded the best calibration curve and sample reads. For that reason, 200 nm is used as the primary peak. All standards and samples were read 3×3 (3 scans of 3 separate aliquots) (Table 5); all data presented is based on averages of the nine readings (FIGS. 15A-B).

TABLE 5

Standard Concentrations of Lucentis in HBSS

| Standard | Concentration (mg/mL) | Absorbance at 278 nm | Absorbance at 220 nm |
|---|---|---|---|
| C0 | 0.125 | 0.301 | 1.273 |
| C1 | 0.100 | 0.219 | 1.025 |
| C2 | 0.0625 | 0.068 | 0.654 |

Eight studies plus a positive and negative control were run in the B-cell (Table 1). For each of the 8 studies, 0.05 mL Lucentis (0.5 mg) was placed in the top chamber for transport through the tissue. The bottom well of the B-cell contains 3 mL HBSS, so the maximum final concentration of drug delivered equals 0.5 mg/3 mL=0.1667 mg/mL. Table 1 lists the concentration and the percent throughout (out of a maximum 0.1667). The positive control was a 0.1667 mg/mL solution placed directly in the bottom B-cell chamber.

Percent throughput varied from a low outlier of 42 percent for the first study to 100 percent for studies 5 and 6. These 100 percent measurements come in at 100.8 and 102.5, suggesting that there is a margin of error around 2.5 to 3 percent. It is also possible that measurements slightly higher than 100 percent could result from traces of additional Lucentis remaining in the B-cell from previous studies.

Statistical analysis showed weak correlations between the parameters and concentrations, with negative correlations for Voltage and Time and a positive correlation for Frequency (Table 6).

TABLE 6

Correlations of Concentrations and Parameters

| Parameter | Correlation |
| --- | --- |
| Voltage | −0.3011 |
| Frequency | 0.404 |
| Time | −0.5636 |

In general, it appears that applying the AC electrical field within the range of times, frequencies, and voltages are effectively transporting the drug through the tissue.

Example 4

Figure 16:
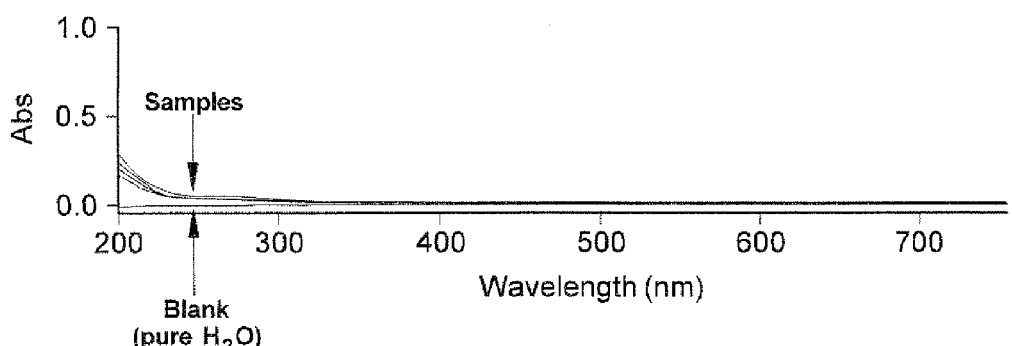
FIG. 16 is a graph showing DEA analysis of a water-based macular degeneration drug (i.e., TIMP-3) in which the water-based drug solutions samples exhibited UV-Vis activity different from that of pure water at wavelengths below 300 nm.

A DEA analysis of a macular degeneration drug, i.e., tissue inhibitor of metalloproteinases-3 (TIMP-3) was tested drug through shedded snake skin at 37° C. for 60 minutes. An interdigitated DEA electrode electrode was rinsed with deionized water and the resulting solution analyzed by UV-Vis spectroscopy to determine whether any of the drug passed through the snake skin to reach the electrode. We were able to identify the critical frequencies and noted that conductivity is very high (e.g., $10^4$), indicating that the drug moves quickly (FIG. 16). Because the drug is a water-based solution, we also ran the same volume of pure water on the snake skin under the same conditions to rule out the possibility that the electrical behavior was due to the water. As shown in FIG. 16, the profile of the pure water sample is radically different from that of the drug and does not show breaks in conductivity at critical frequencies. Successful delivery of the drug through snake skin in the DEA has proven to be a good predictor of successful drug transport using the interdigitated electrodes.

From the above description of the invention, those skilled in the art will perceive improvements, changes and modifications. Such improvements, changes, and modifications are within the skill of the art and are intended to be covered by the appended claims.

Having described the invention, we claim:

1. An apparatus for delivering at least one therapeutic agent to an ocular tissue of a subject, said apparatus comprising:
at least one electrode having oppositely disposed, dome-shaped first and second electrically-conductive major surfaces, said first major surface being curved such that said first major surface substantially conforms to a contour of the ocular tissue when said first major surface is in contact with the ocular tissue;
a medicament layer including the at least one therapeutic agent, said medicament layer being disposed on at least a portion of said second major surface;
an electrical signal source for providing a signal having certain characteristics, said electrical signal source being electrically connected to said at least one electrode;
logic configured to control said electrical signal source;
wherein said certain characteristics of said electrical signal source comprise at least one orienting frequency and at least one motivating frequency sufficient to motivate the at least one therapeutic agent into the ocular tissue; and
a positioning member for placing at least a portion of said first major surface into contact with the ocular tissue, said positioning member comprising a clam-shaped housing, said housing comprising:
a first opposable member;
a second opposable member;
a hinge mechanism operably connecting said first opposable member with said second opposable member; and
a securing mechanism for mating said first opposable member with said second opposable member;
wherein said at least one electrode is securely seated within said housing.

2. The apparatus of claim 1, wherein each of said at least one orienting frequency and said at least one motivating frequency comprises an alternating current (AC) signal.

3. The apparatus of claim 1, wherein said at least one orienting frequency comprises an alternating current (AC) signal and said at least one motivating frequency comprises a direct current (DC) signal.

4. The apparatus of claim 1, wherein said at least one electrode is an interdigitated electrode.

5. The apparatus of claim 1, wherein said first major surface of said at least one electrode is curved such that said first major surface is substantially similar to a radius of curvature of a human eye.

6. The apparatus of claim 1, wherein each of said first and second opposable members is ring-shaped and includes a central opening, said at least one electrode being securely seated within said central opening of said first opposable member.

7. The apparatus of claim 6, wherein said second opposable member includes a dome-shaped member securely seated within said central opening thereof.

8. A system for delivering at least one therapeutic agent to an ocular tissue of a subject, said system comprising:
an apparatus including:
at least one electrode having oppositely disposed, dome-shaped first and second electrically-conductive major surfaces, said first major surface being curved such that said first major surface substantially conforms to a contour of the ocular tissue when said first major surface is in direct contact with the ocular tissue;
a medicament layer including the at least one therapeutic agent, said medicament layer being disposed on at least a portion of said second major surface;
an electrical signal source for providing a signal having certain characteristics, said electrical signal source being electrically connected to said at least one electrode;
logic configured to control said electrical signal source;
wherein said certain characteristics of said electrical signal source comprise at least one orienting frequency and at least one motivating frequency sufficient to motivate the at least one therapeutic agent into the ocular tissue;

an electrical lead having oppositely disposed proximal and distal ends, said proximal end being electrically connected to said electrical signal source and said distal end being electrically connected to said at least one electrode, said electrical lead for delivering said signal to said at least one electrode; and a displacement device for facilitating application of said first major surface of said at least one electrode to the ocular tissue, said displacement device being securely connected to said electrical lead, said displacement device comprising:

oppositely disposed, flexible first and second arm members, each of said arm members including a distal end portion and a proximal end portion, said distal end portion of each of said first and second arm members including first and second channels for receiving at least a portion of an upper eyelid and a lower eyelid, respectively; and a connection member operably joining said proximal end portion of each of said first and second arm members and said electrical lead.

* * * * *